US012779116B2

(12) United States Patent
Nichols et al.

(10) Patent No.: US 12,779,116 B2
(45) Date of Patent: Nov. 3, 2026

(54) SYSTEMS AND METHODS FOR PROCESSING CONTINUOUS GLUCOSE MONITOR VALUES IN AUTOMATED INSULIN DELIVERY

(71) Applicant: Tandem Diabetes Care, Inc., San Diego, CA (US)

(72) Inventors: Brendan Nichols, San Diego, CA (US); Paul Harris, San Diego, CA (US); Jose Ricardo Rueda, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 1031 days.

(21) Appl. No.: 17/878,681

(22) Filed: Aug. 1, 2022

(65) Prior Publication Data

US 2023/0034408 A1 Feb. 2, 2023

Related U.S. Application Data

(60) Provisional application No. 63/228,468, filed on Aug. 2, 2021.

(51) Int. Cl.
*A61M 5/172* (2006.01)
*A61M 5/142* (2006.01)

(52) U.S. Cl.
CPC ...... *A61M 5/1723* (2013.01); *A61M 5/14244* (2013.01); *A61M 2205/50* (2013.01); *A61M 2230/201* (2013.01)

(58) Field of Classification Search
CPC ............ A61M 5/1723; A61M 5/14244; A61M 2205/50; A61M 2230/201
See application file for complete search history.

(56) References Cited

U.S. PATENT DOCUMENTS 4,757,022 A * 7/1988 Shults .................. A61B 5/1486 204/403.05
4,787,398 A * 11/1988 Garcia ............... A61B 5/15194 600/583
5,497,772 A * 3/1996 Schulman ............ A61B 5/1495 600/347

(Continued)

FOREIGN PATENT DOCUMENTS

EP 2905711 A1 8/2015
JP 2014-524294 A 9/2014

OTHER PUBLICATIONS

European Search Report for related European Patent Application No. 22853773, mailed Mar. 19, 2025, 10 pages.

(Continued)

*Primary Examiner* — Cris L. Rodriguez
(74) *Attorney, Agent, or Firm* — Straylight LLP

(57) ABSTRACT

Disclosed herein are systems and methods incorporating an ambulatory infusion pump and a CGM. These systems that can include software and related methods to provide improved automated insulin delivery algorithms that combine and/or filter CGM readings. Embodiments disclosed herein can combine and/or filter additional CGM readings received between therapy calculations by the algorithm to provide improved and more accurate insulin delivery. Methods can include filtering and/or combining CGM readings for a current dosing interval and/or or for past dosing intervals that are used to generate a predicted future glucose level to inform dosing.

20 Claims, 5 Drawing Sheets

(56) References Cited

U.S. PATENT DOCUMENTS

| | | | | |
|---|---|---|---|---|
| 6,001,067 | A * | 12/1999 | Shults | A61B 5/14865 600/584 |
| 9,452,258 | B2 | 9/2016 | Dobbles | |
| 10,130,767 | B2 * | 11/2018 | Grosman | G16H 20/17 |
| 10,154,804 | B2 * | 12/2018 | Steil | A61K 38/28 |
| 2005/0027463 | A1 * | 2/2005 | Goode, Jr. | A61B 5/1433 702/22 |
| 2005/0203360 | A1 * | 9/2005 | Brauker | A61B 5/7275 600/345 |
| 2011/0237917 | A1 * | 9/2011 | Roy | A61B 5/1495 600/365 |
| 2013/0041343 | A1 | 2/2013 | Toumazou et al. | |
| 2013/0338630 | A1 | 12/2013 | Agrawal et al. | |
| 2014/0066887 | A1 * | 3/2014 | Mastrototaro | A61B 5/4839 604/506 |
| 2014/0180203 | A1 * | 6/2014 | Budiman | A61B 5/4839 604/66 |
| 2015/0351673 | A1 * | 12/2015 | Vanslyke | A61B 5/1473 600/301 |
| 2018/0303389 | A1 | 10/2018 | Sloan et al. | |
| 2019/0392937 | A1 | 12/2019 | Mensinger et al. | |
| 2021/0113766 | A1 * | 4/2021 | Kearns | G16H 40/63 |
| 2022/0386905 | A1 * | 12/2022 | Jacobs | G16H 50/50 |

OTHER PUBLICATIONS

International Preliminary Report on Patentability and Written Opinion issued Feb. 6, 2024 for International Patent Application No. PCT/US2022/039065.

Notification of International Preliminary Report on Patentability and Written Opinion issued Feb. 15, 2024 for International Patent Application No. PCT/US2022/039065.

International Search Report issued Nov. 21, 2022 for International Patent Application No. PCT/US2022/039065.

Keenan, et al., "Delays in Minimally Invasive Continuous Glucose Monitoring Devices: A Review of Current Technology", Sep. 2009, Journal of Diabetes Science and Technology, vol. 3, Issue 5, p. 1207-1214.

Office Action issued Mar. 13, 2024 for European Patent Application No. 22853773.4.

* cited by examiner

SYSTEMS AND METHODS FOR PROCESSING CONTINUOUS GLUCOSE MONITOR VALUES IN AUTOMATED INSULIN DELIVERY

RELATED APPLICATION

The present application claims the benefit of U.S. Provisional Application No. 63/228,468, filed Aug. 2, 2021, which is hereby incorporated herein in its entirety by reference.

FIELD OF THE INVENTION

The present invention relates generally to ambulatory infusion pumps and, more particularly, to operation of ambulatory infusion pumps in a closed-loop or semi-closed-loop fashion.

BACKGROUND OF THE INVENTION

There are a wide variety of medical treatments that include the administration of a therapeutic fluid in precise, known amounts at predetermined intervals. Devices and methods exist that are directed to the delivery of such fluids, which may be liquids or gases, are known in the art.

One category of such fluid delivery devices includes insulin injecting pumps developed for administering insulin to patients afflicted with type 1, or in some cases, type 2 diabetes. Some insulin injecting pumps are configured as portable or ambulatory infusion devices that can provide continuous subcutaneous insulin injection and/or infusion therapy as an alternative to multiple daily insulin injections via syringe or injector pen. Such ambulatory infusion pumps may be worn by the user, may use replaceable medicament cartridges, and may deliver other medicaments alone, or in combination with insulin. Such medicaments include glucagon, pramlintide, and the like. Examples of such pumps and various features associated therewith include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

Ambulatory infusion pumps for delivering insulin or other medicaments can be used in conjunction with blood glucose monitoring systems, such as continuous glucose monitoring (CGM) devices. A CGM device consists of a sensor placed under the patient's skin and affixed to the patient via an adhesive patch, a transmitter, and a monitor. A CGM device samples the patient's interstitial fluid periodically (e.g. once every 1-5 minutes) to estimate blood glucose levels over time. CGMs are advantageous because they provide more frequent insights into a user's blood glucose levels yet do not require a finger stick each time a reading is taken.

Ambulatory infusion pumps may incorporate a CGM within the hardware of the pump or may communicate with a dedicated CGM directly via a wired connection or indirectly via a wireless connection using wireless data communication protocols to communicate with a separate device (e.g., a dedicated remote device or a smartphone). One example of integration of ambulatory infusion pumps with CGM devices is described in U.S. Patent Publication No. 2014/0276419, which is hereby incorporated by reference herein. Ambulatory infusion pumps typically allow the user or caregiver to adjust the amount of insulin or other medicament delivered by a basal rate or a bolus, based on blood glucose data obtained by a CGM device, and in some cases include the capability to automatically adjust such medicament delivery. For example, based on CGM readings, some ambulatory infusion pumps may automatically adjust or prompt the user to adjust the level of medicament being administered or planned for administration or, in cases of abnormally low blood glucose readings, reducing or temporarily ceasing insulin administration.

In some cases, ambulatory insulin pumps may be configured to deliver insulin based on CGM data in a closed-loop or semi-closed-loop fashion. Some systems including these features may be referred to as automated insulin delivery (AID) systems or artificial pancreas systems because these systems serve to mimic biological functions of the pancreas for persons with diabetes. In such systems, CGM sensors measure glucose levels and send the readings to the pump at a set interval. These closed loop algorithms are similarly configured to make therapy decisions at set intervals.

SUMMARY

Disclosed herein are systems and methods incorporating an ambulatory infusion pump and a CGM. These systems that can include software and related methods to provide improved automated insulin delivery algorithms that combine and/or filter CGM readings. Embodiments disclosed herein can combine and/or filter additional CGM readings received between therapy calculations by the algorithm to provide improved and more accurate insulin delivery. Methods can include filtering and/or combining CGM readings for a current dosing interval and/or or for past dosing intervals that are used to generate a predicted future glucose level to inform dosing.

In an embodiment, an ambulatory infusion pump system can include a pump mechanism configured to facilitate delivery of insulin to a user, a communications device adapted to receive glucose levels from a continuous glucose monitor data intervals and at least one processor functionally linked to the pump mechanism and the communications device. The at least one processor can be configured to automatically calculate insulin doses with a closed loop delivery algorithm based on the glucose levels received from the continuous glucose monitor with a time between calculating insulin doses that may be longer than the data intervals between receiving glucose levels from the continuous glucose monitor. The calculated insulin doses can then be automatically delivered with the pump mechanism. Automatically calculating insulin doses based on the glucose levels received from the continuous glucose monitor can include combining and/or filtering a plurality of glucose levels received during the time between each dosing calculation.

In an embodiment, a method of diabetes therapy includes receiving glucose levels from a continuous glucose monitor, automatically calculating insulin doses with a closed loop delivery algorithm based on the glucose levels received from the continuous glucose monitor such that a time between calculating insulin doses may be longer than the time between receiving glucose levels from the continuous glucose monitor and automatically delivering the insulin doses calculated by the closed loop delivery algorithm with the pump mechanism. Automatically calculating insulin doses based on the glucose levels received from the continuous glucose monitor can include at least one of combining and filtering a plurality of glucose levels received during the time between each dosing interval.

BRIEF DESCRIPTION OF THE DRAWINGS

The invention may be more completely understood in consideration of the following detailed description of various embodiments of the invention in connection with the accompanying drawings, in which.

Figure 1:
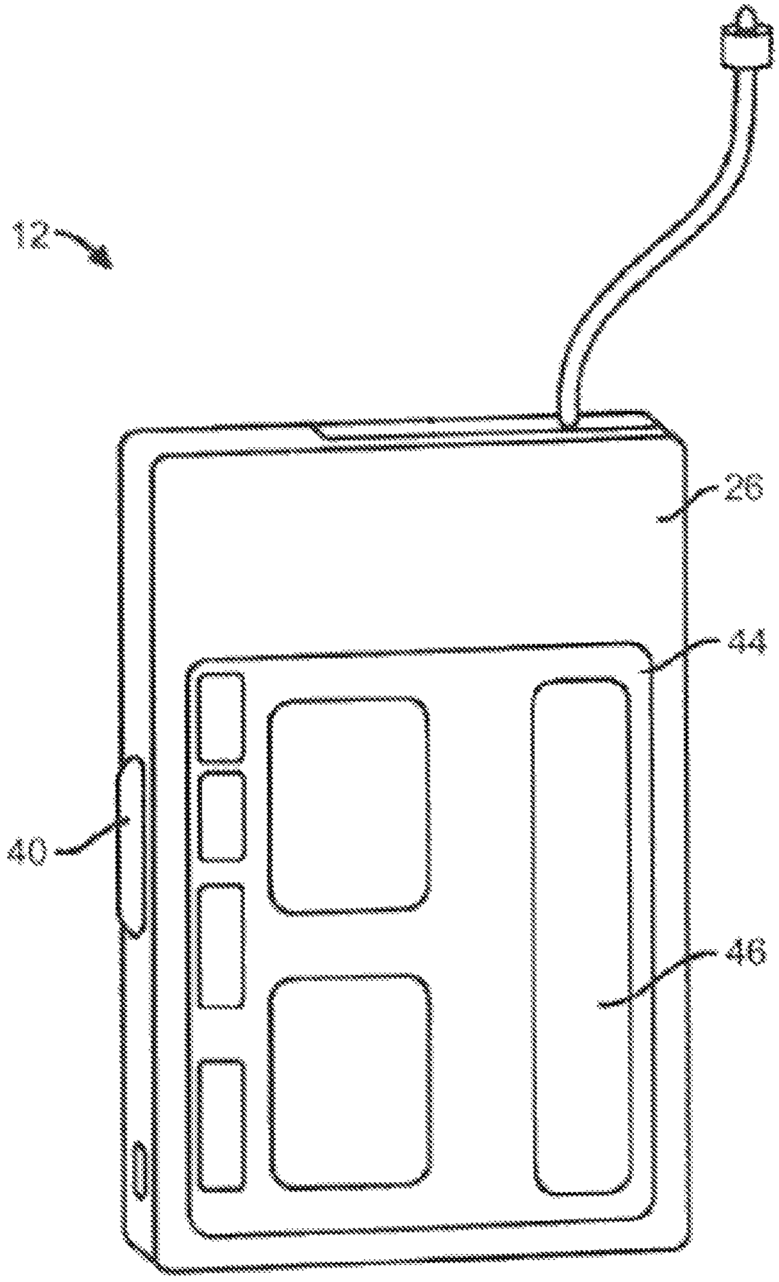
FIG. 1 is an embodiment of an ambulatory infusion pump for use with embodiments of the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

FIG. 1 depicts an example infusion pump that can be used in conjunction with one or more embodiments of the ambulatory infusion pump system of the present disclosure. Pump 12 includes a pumping or delivery mechanism and reservoir for delivering insulin or other medicament to a patient and an output/display 44. The output/display 44 may include an interactive and/or touch sensitive screen 46 having an input device such as, for example, a touch screen comprising a capacitive screen or a resistive screen. The pump 12 may additionally or instead include one or more of a keyboard, a microphone or other input devices known in the art for data entry, some or all of which may be separate from the display. The pump 12 may also include a capability to operatively couple to one or more other display devices such as a remote display (e.g., a dedicated remote display or a CGM display), a remote control device, or a consumer electronic device (e.g., laptop computer, personal computer, tablet computer, smartphone, electronic watch, electronic health or fitness monitor, or personal digital assistant). Further details regarding such pump devices can be found in U.S. Pat. No. 8,287,495, previously incorporated by reference above. It is to be appreciated that pump 12 may be optionally configured to deliver one or more additional or other medicaments to a patient.

Figure 2:
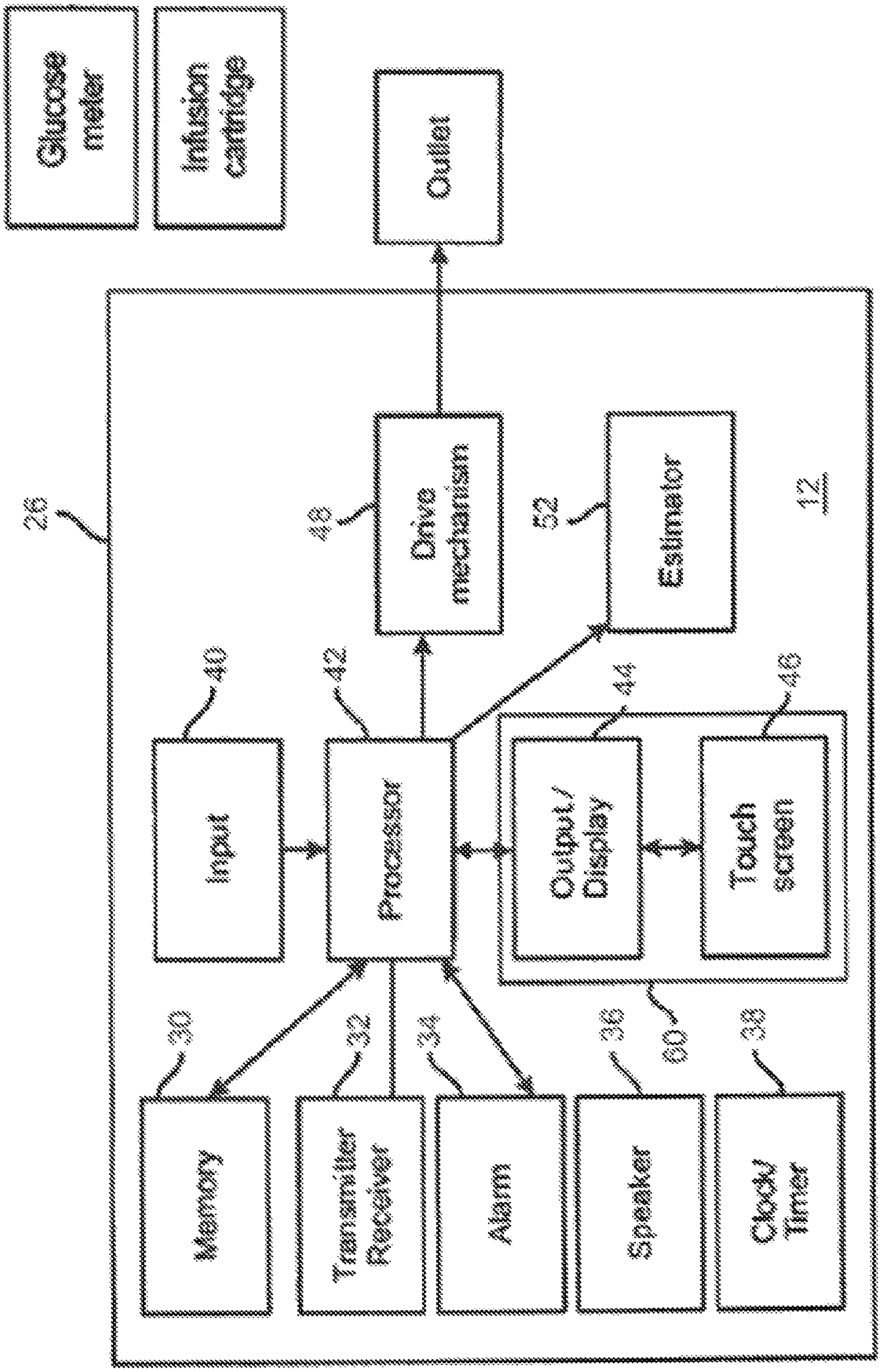
FIG. 2 is a block diagram of the ambulatory infusion pump of FIG. 1.

FIG. 2 illustrates a block diagram of some of the features that may be included within the housing 26 of pump 12. The pump 12 can include a processor 42 that controls the overall functions of the pump. The pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface is a graphical user interface (GUI) 60 having a touch sensitive screen 46 with input capability. In some embodiments, the processor 42 may communicate with one or more other processors within the pump 12 and/or one or more processors of other devices through the transmitter/receiver 32 such as a remote device (e.g., CGM device), a remote control device, or a consumer electronic device (e.g., laptop computer, personal computer, tablet computer, smartphone, electronic watch, electronic health or fitness monitor, or personal digital assistant). In some embodiments, the communication is effectuated wirelessly, by way of example only, via a near field communication (NFC) radio frequency (RF) transmitter or a transmitter operating according to a "Wi-Fi" or Bluetooth® protocol, Bluetooth® low energy protocol or the like. The processor 42 may also include programming to receive signals and/or other data from an input device, such as, by way of example, a pressure sensor, a temperature sensor, or the like.

Figure 3B:
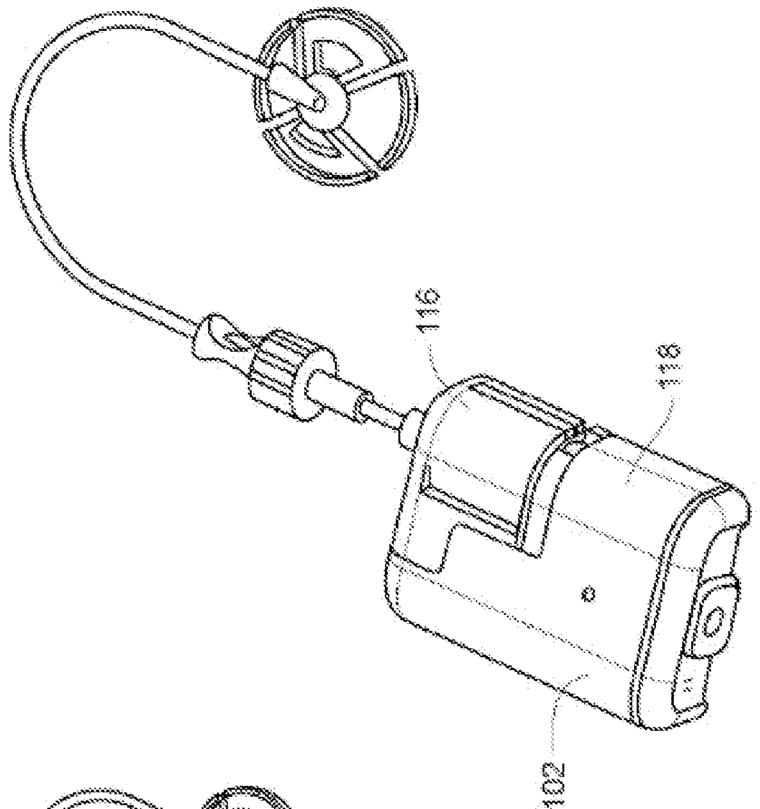
FIGS. 3A-3B are an alternate embodiment of an ambulatory infusion pump for use with embodiments of the disclosure.
Figure 3A:
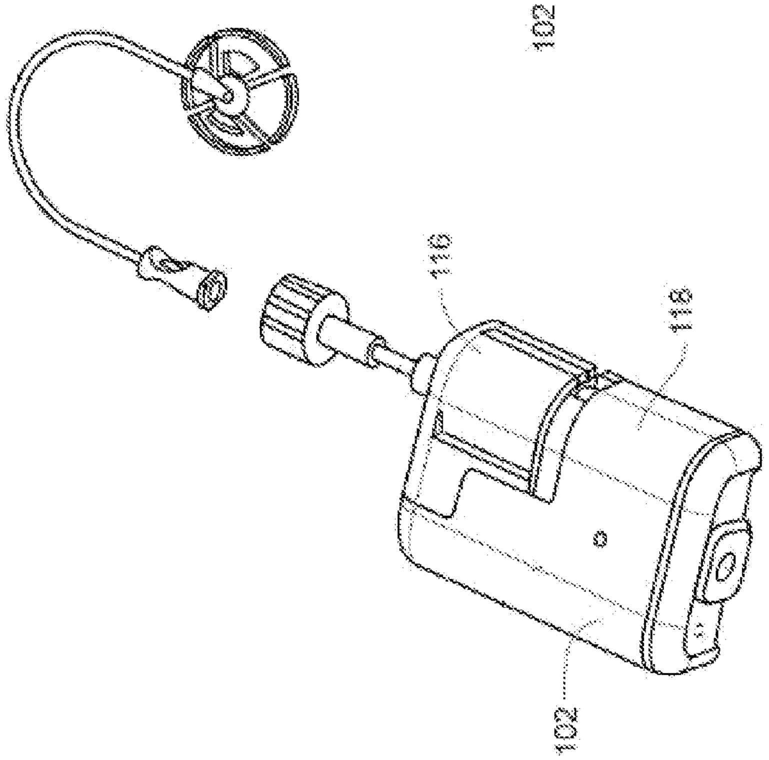

FIGS. 3A-3B depicts a second infusion pump that can be used in conjunction with one or more embodiments of the ambulatory infusion pump system of the present disclosure. Pump 102 includes a pump drive unit 118 and a medicament cartridge 116. Pump 102 includes a processor that may communicate with one or more processors within the pump 102 and/or one or more processors of other devices such as a remote device (e.g., a CGM device), a remote control device, or a consumer electronic device (e.g., laptop computer, personal computer, tablet computer, smartphone, electronic watch, electronic health or fitness monitor, or personal digital assistant). The processor 42 may also include programming to receive signals and/or other data from an input device, such as, by way of example, a pressure sensor, a temperature sensor, or the like. Pump 102 also includes a processor that controls some or all of the operations of the pump. In some embodiments, pump 102 receive commands from a separate device for control of some or all of the operations of the pump. Such separate device can include, for example, a dedicated remote control device or a consumer electronic device such as a smartphone having a processor executing an application configured to enable the device to transmit operating commands to the processor of pump 102. In some embodiments, processor can also transmit information to one or more separate devices, such as information pertaining to device parameters, alarms, reminders, pump status, etc. Such separate device can include any remote display, remote control device, or a consumer electronic device as described above. Pump 102 can also incorporate any or all of the features described with respect to pump 12 in FIG. 2. In some embodiments, the communication is effectuated wirelessly, by way of example only, via a near field communication (NFC) radio frequency (RF) transmitter or a transmitter operating according to a "Wi-Fi" or Bluetooth® protocol, Bluetooth® low energy protocol or the like. Further details regarding such pumps can be found in U.S. Pat. No. 10,279,106 and U.S. Patent Publication Nos. 2016/0339172 and 2017/0049957, each of which is hereby incorporated herein by reference in its entirety.

Figure 4:
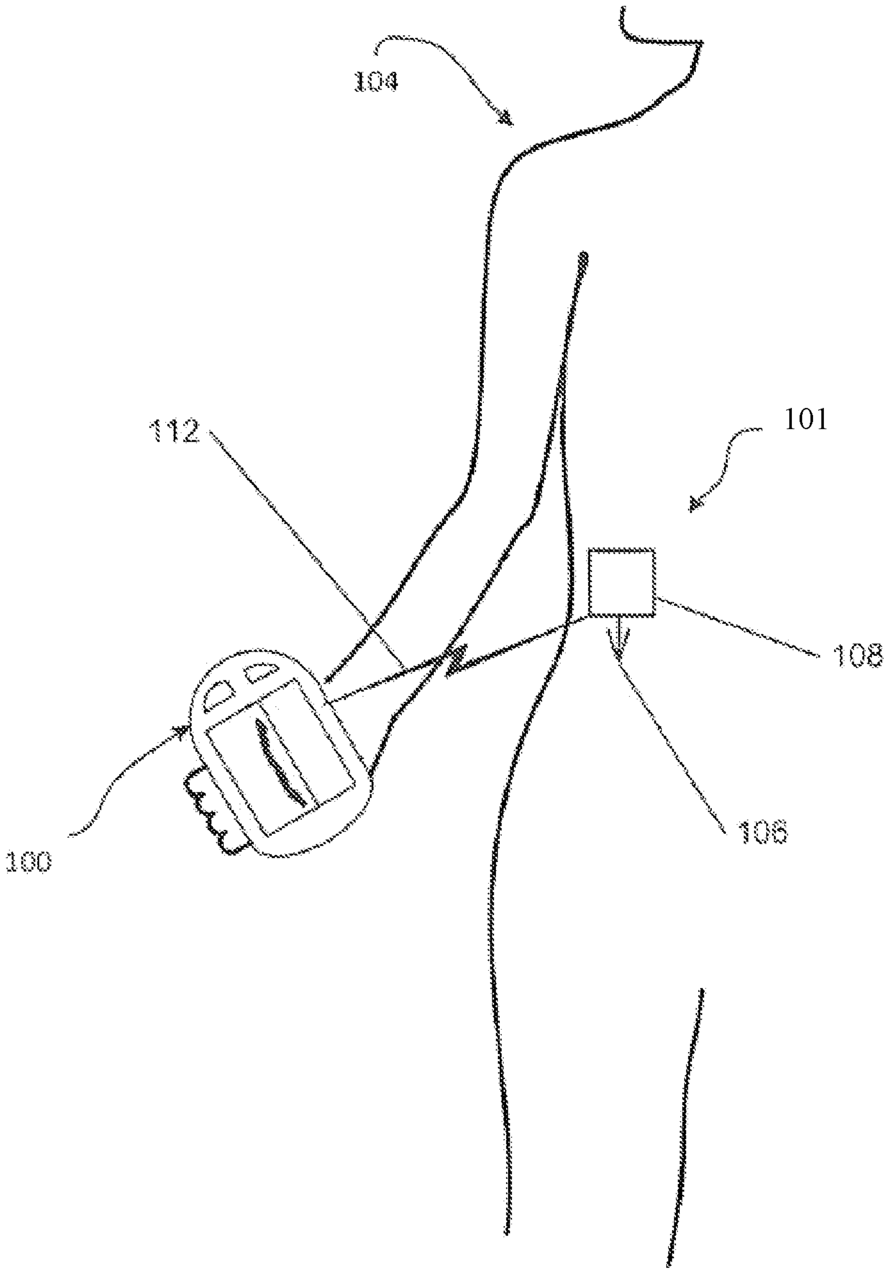
FIG. 4 is an embodiment of a CGM for use with embodiments of the disclosure.

FIG. 4 depicts an example CGM system that can be used in conjunction with one or more embodiments of the ambulatory infusion pump system of the present disclosure. The CGM system includes a sensor 101, a sensor probe 106, a sensor body 108, a receiver, and a monitor (receiver and monitor are depicted as device 100 in FIG. 4). The sensor 101 is removably affixed to a user 104 and includes a sensor probe 106 configured for transcutaneous insertion into the user 104. When placed, the sensor probe 106 reacts with the user's interstitial fluid which produces a signal that can be associated with the user's blood glucose level. The sensor 101 further includes a sensor body 108 that transmits data associated with the signal to the receiver 100 via wired or wireless connection (as represented by arrow line 112). In preferred embodiments, the receiver 100 receives the transmitted data wirelessly by any suitable means of wireless communication. By way of example only, this wireless communication may include a near field communication (NFC) radio frequency (RF) transmitter or a transmitter operating according to a "Wi-Fi" or Bluetooth® protocol, Bluetooth® low energy protocol or the like. Further detail regarding such systems and definitions of related terms can be found in, e.g., U.S. Pat. Nos. 8,311,749, 7,711,402 and 7,497,827, each of which is hereby incorporated by reference in its entirety.

With the infusion pump and CGM interfaced, the CGM can automatically transmit the CGM data to the pump. The pump can then use this data to automatically determine therapy parameters and suggest a therapy adjustment to the user or automatically deliver the therapy adjustment to the user. These therapy parameters including thresholds and target values can be stored in memory located in the pump or, if not located in the pump, stored in a separate location and accessible by the pump processor (e.g., "cloud" storage, a smartphone, a CGM, a dedicated controller, a computer, etc., any of which is accessible via a network connection). The pump processor can periodically and/or continually execute instructions for a checking function that accesses these data in memory, compares them with data received from the CGM and acts accordingly to adjust therapy. In further embodiments, rather than the pump determining the therapy parameters, the parameters can be determined by a separate device and transmitted to the pump for execution. In such embodiments, a separate device such as the CGM or a device in communication with the CGM, such as, for example, a smartphone, dedicated controller, electronic tablet, computer, etc. can include a processor programmed to calculate therapy parameters based on the CGM data that then instruct the pump to provide therapy according to the calculated parameters.

For example, if the CGM readings indicate that the user has or is predicted to have a high blood glucose level (hyperglycemia), the ambulatory infusion system can automatically calculate an insulin dose sufficient to reduce the user's blood glucose level below a threshold level or to a target level and automatically deliver the dose. Alternatively, the ambulatory infusion system can automatically suggest a change in therapy upon receiving the CGM readings such as an increased insulin basal rate or delivery of a bolus, but can require the user to accept the suggested change prior to delivery rather than automatically delivering the therapy adjustments.

By way of further example, if the CGM readings indicate that the user has or is predicted to have a low blood glucose level (hypoglycemia), the ambulatory infusion system can, for example, automatically reduce or suspend a basal rate, suggest to the user to reduce a basal rate, automatically deliver or suggest that the user initiate the delivery of an amount of a substance such as, e.g., a hormone (glucagon) to raise the concentration of glucose in the blood, automatically suggest that the patient address the hypoglycemic condition as necessary (e.g., ingest carbohydrates), singly or in any desired combination or sequence. Such determination can be made by the infusion pump providing therapy or by a separate device that transmits therapy parameters to the infusion pump. In some embodiments, multiple medicaments can be employed in such an ambulatory infusion system as, for example, a first medicament, e.g., insulin, that lowers blood glucose levels and a second medicament, e.g., glucagon, that raises blood glucose levels.

Automated insulin delivery (AID) systems such as those described above are configured to periodically receive glucose levels from the CGM at a fixed or variable interval and also operate an algorithm that periodically makes dosing decisions at a fixed or variable interval. Many CGMs provide a new glucose reading every 5 minutes and therefore some closed loop algorithms also calculate dosing every 5 minutes. However, some CGM technology has been configured to send a new glucose level reading more frequently, such as every minute. If new readings are received more frequently, e.g., every minute, than the control algorithm makes dosing decisions, e.g., every 5 minutes or any varying time in which multiple readings are received between doses, there is an opportunity to use the additional data to make better informed dosing decisions. As noted above, while in some embodiments doses are calculated and/or CGM readings received at fixed intervals, in some embodiments doses need not be calculated and/or CGM readings may not be received at fixed intervals.

Embodiments disclosed herein therefore combine and/or filter additional CGM readings to provide improved and more accurate insulin delivery. Methods can include filtering and/or combining CGM readings for a current dosing interval and/or or for past dosing intervals that are used to generate a predicted glucose level in the future to inform dosing. In such embodiments, past dosing intervals provide the advantage of having CGM data from both before and after the dosing interval.

In embodiments, CGM readings can be combined for a current dosing interval by averaging all CGM data points received since the last dosing interval, rather than using only the most recent reading received at the time of the dosing interval. Readings can be combined using various methods, such as, for example, with a simple moving average (i.e., the mean level of the data points), a weighted moving average (i.e., giving higher weight to certain data points) or an exponential moving average (i.e., applying weighting factors that decrease/increase exponentially). For weighted and exponential moving averages, greater weight can be given to CGM readings that are closer in time to the current dosing interval.

CGM readings for a current dosing interval can in embodiments be combined by fitting a trend line to the CGM readings received since the last dosing interval. In some embodiments, the readings can further be filtered by omitting any readings that deviate significantly from the trend before combining readings. The value used for the therapy calculation can be either the current reading if it fits with the trend or a value can be estimated based on the trend line. Similarly, if the most recent reading does not align with the trend, the estimated glucose value can be determined from the trend and used in place of or combined with the most recent reading.

Some embodiments can limit the rate of change in glucose values based on physiological inputs to the algorithm such as weight, total daily insulin, insulin sensitivity factor, carbohydrate ratio and/or insulin action time. In embodiments, CGM readings for a current dosing interval can be filtered using an infinite impulse response (IIR) filter. Various other filtering techniques could also be applied, such as, for example, finite impulse response (FIR) filtering, slew rate limiting, etc. Such embodiments create a system that is personalized to the user's physiology. Physiologic inputs can alternatively or additionally be used to omit glucose values that are not physiologically possible.

CGM readings for a current dosing interval can additionally or alternatively be filtered using trend information provided by the CGM to limit the magnitude of change between CGM readings according to some embodiments. For example, if trend information provided by the CGM on the previous reading was a rate of increase of +3 mg/dL/minute, the magnitude of change of the current reading would be limited to greater than or equal to 0 mg/dL/minute due to the unlikelihood of the rate of change significantly reversing.

For past dosing intervals, in some embodiments CGM readings can be combined by averaging CGM readings received immediately before and immediately after the past dosing interval. Readings can be combined using, for example, a simple moving average, a weighted moving average or an exponential moving average. For weighted and exponential averaging, greater weight can be given to CGM readings closer to the dosing interval. The revised glucose level determined using the previous and subsequent measurements can then be used in place of or combined with the actual measurement at the time of the dosing interval in calculating predicted future glucose levels.

CGM readings for past dosing intervals could also be combined by applying clamped cubic spline interpolation on historical readings to generate a smooth curve fit to the historical data. The glucose level on the curve corresponding to the time of the past dosing interval could be used in place of or combined with the actual reading recorded at that time for use in determining future doses.

In some embodiments, CGM readings for past dosing intervals can be filtered by fitting a trend line to the CGM readings before and after the dosing interval. Readings that deviate significantly from the trend line can be omitted before combining the readings to update the reading used for a predicted glucose level. Alternatively, the actual reading used for a given dosing interval can be used in future calculations if the reading fits the trend line. If the reading is not a good fit with the trend line, the reading can be discarded and the estimated value from the trend line can be used instead or combined with the reading.

Figure 5:
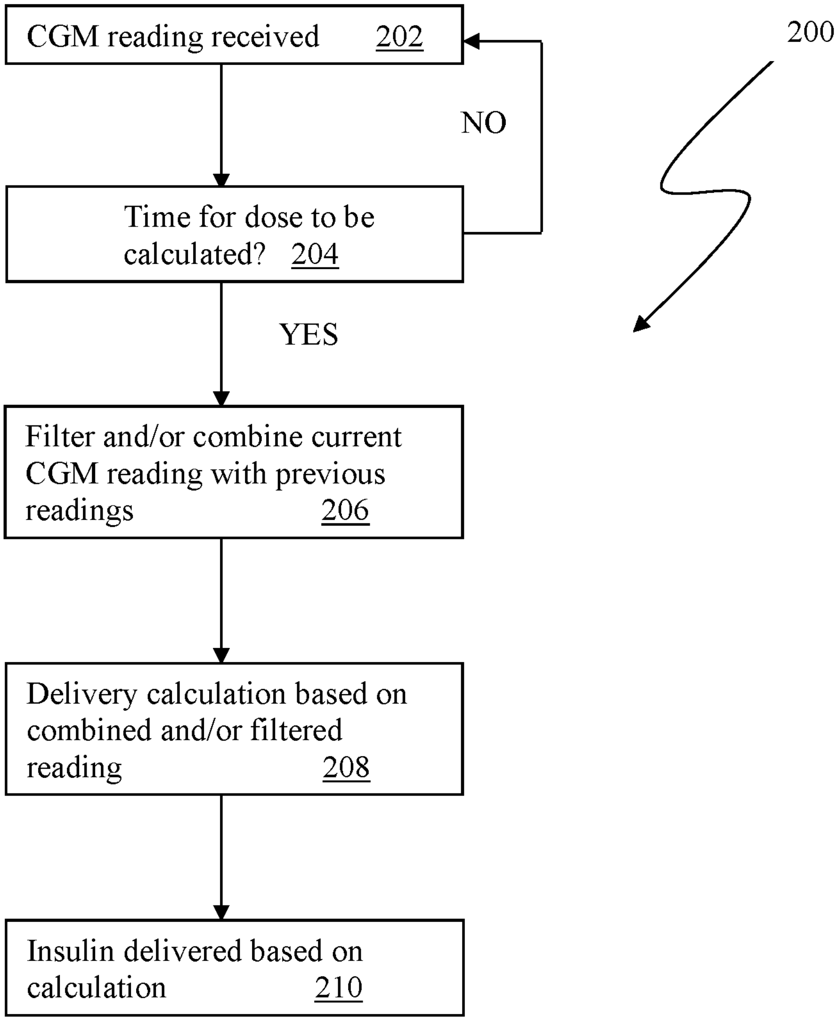
FIG. 5 is a flowchart of a method of medicament delivery utilizing a closed loop delivery algorithm according to the disclosure.

Referring now to FIG. 5, a flowchart of a method of medicament delivery utilizing a closed loop delivery algorithm 200 according to the disclosure is depicted. At step 202, a glucose level reading is received from a CGM. When the reading is received, it is determined at step 204 if it is time for the closed loop algorithm to calculate a therapy dose and/or an adjustment to an ongoing therapy for delivery to the user. If not, the system awaits the next reading at step 202 and performs the same determination at step 204 after the next reading is received. If it is time for a therapy calculation, the system can combine and/or filter the current reading along with the previous readings since the last therapy calculation at step 206 using any of the methods described herein. For example, in a system that makes therapy calculations every five minutes and receives a glucose level reading every minute, otherwise has received multiple glucose levels readings since the previous therapy calculation, the current reading can be combined and/or filtered with the other readings received since the previous calculation. In some embodiments, in systems that utilize predicted future glucose levels in making dosing decisions, the system can further refine the glucose level used for dosing by updating the glucose levels used at past dosing intervals based on subsequently received CGM readings as set forth above. An insulin dose can be calculated and/or an ongoing delivery of insulin modified according to the combined and/or filtered glucose level at step 208. Insulin can then be delivered and/or modified according to the calculation at step 210.

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed decription.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357,603; 10,357,606; 10,492,141; 10/541,987; 10,569,016; 10,736,037; 10,888,655; 10,994,077; 11,116,901; 11,224,693; 11,291,763; and 11,305,057 and commonly owned U.S. Patent Publication Nos. 2009/0287180; 2012/0123230; 2013/0053816; 2014/0276423; 2014/0276569; 2014/0276570; 2018/0071454; 2019/0240398; 2019/0307952; 2020/0206420; 2020/0261649; 2020/0329433; 2020/0368430; 2020/0372995; 2021/0001044; 2021/0113766; 2021/0154405; 2021/0353857; 2022/0062553; 2022/0139522 and 2022/0223250 and commonly owned U.S. patent application Ser. Nos. 17/368,968; 17/587,412; 17/587,434; 17/587,468; 17/677,621; 17/729,464; and Ser. No. 17/732,208.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. An ambulatory infusion pump system, comprising:
   - a pump mechanism configured to facilitate delivery of insulin to a user;
   - a communications module adapted to receive glucose levels from a continuous glucose monitor at a data interval;
   - at least one processor functionally linked to the pump mechanism and the communications module, wherein the at least one processor is configured to:
     - automatically calculate insulin doses with a closed-loop delivery algorithm based on the glucose levels received from the continuous glucose monitor, the closed-loop delivery algorithm calculating insulin doses at a dosing interval that is longer than the data interval such that a plurality of glucose levels are received from the continuous glucose monitor between consecutive dosing calculations; and
     - automatically deliver the insulin doses calculated by the closed-loop delivery algorithm with the pump mechanism,
     - wherein automatically calculating insulin doses based on the glucose levels received from the continuous glucose monitor for a current dosing calculation includes the closed-loop delivery algorithm performing at least one of combining and filtering the plurality of glucose levels received from the continuous glucose monitor since a previous dosing calculation.

2. The ambulatory infusion pump system of claim 1, wherein the at least one processor is further configured to average the plurality of glucose levels received since the previous dosing calculation and to utilize the average in the current dosing calculation.

3. The ambulatory infusion pump system of claim 1, wherein the at least one processor is further configured to filter the plurality of glucose levels by eliminating glucose levels that deviate significantly from other glucose levels in calculating insulin doses.

4. The ambulatory infusion pump system of claim 3, wherein the at least one processor is further configured to fit a trend line to the plurality of glucose levels and determine which glucose levels deviate significantly based on the trend line.

5. The ambulatory infusion pump system of claim 1, wherein the at least one processor is further configured to fit a trend line to the plurality of glucose levels for determining a glucose level to use in the current dosing calculation.

6. The ambulatory infusion pump system of claim 5, wherein the glucose level used in the current dosing calculation is estimated based on the trend line.

7. The ambulatory infusion pump system of claim 5, wherein the glucose level used in the current dosing calculation is a most recent glucose level that fits the trend line.

8. The ambulatory infusion pump system of claim 1, wherein the at least one processor is further configured to filter the plurality of glucose levels using an infinite impulse response filter.

9. The ambulatory infusion pump system of claim 1, wherein the at least one processor is further configured to filter the plurality of glucose levels by omitting glucose levels that are not physiologically possible in calculating insulin doses.

10. The ambulatory infusion pump system of claim 9, wherein:
    - the at least one processor is further configured to receive one or more physiological parameters of the user comprising one or more of a weight of the user, a total daily insulin of the user, an insulin sensitivity factor of the user, a carbohydrate ratio of the user, and an insulin action time of the user; and
    - omitting the glucose levels that are not physiologically possible is based on the one or more physiological parameters of the user.

11. A method of diabetes therapy, comprising:
    - receiving glucose levels from a continuous glucose monitor at a data interval;
    - automatically calculating insulin doses with a closed-loop delivery algorithm based on the glucose levels received from the continuous glucose monitor, the closed-loop delivery algorithm calculating insulin doses at a dosing interval that is longer than the data interval such that a plurality of glucose levels are received from the continuous glucose monitor between consecutive dosing calculations; and
    - automatically delivering the insulin doses calculated by the closed-loop delivery algorithm with a pump mechanism,
    - wherein automatically calculating insulin doses based on the glucose levels received from the continuous glucose monitor for a current dosing calculation includes the closed-loop delivery algorithm performing at least one of combining and filtering the plurality of glucose levels received from the continuous glucose monitor since a previous dosing calculation.

12. The method of claim 11, wherein combining the plurality of glucose levels includes averaging the plurality of glucose levels received since the previous dosing calculation and further comprising utilizing the average in the current dosing calculation.

13. The method of claim 11, wherein filtering the plurality of glucose levels includes eliminating glucose levels that deviate significantly from other glucose levels in calculating insulin doses.

14. The method of claim 13, further comprising fitting a trend line to the plurality of glucose levels and determining which glucose levels deviate significantly based on the trend line.

15. The method of claim 11, further comprising fitting a trend line to the plurality of glucose levels for determining a glucose level to use in the current dosing calculation.

16. The method of claim 15, further comprising using a most recent glucose level in the current dosing calculation that fits the trend line.

17. The method of claim 15, further comprising estimating the glucose level used in the current dosing calculation based on the trend line.

18. The method of claim 11, wherein filtering the plurality of glucose levels includes using an infinite impulse response filter.

19. The method of claim 11, wherein filtering the plurality of glucose levels includes omitting glucose levels that are not physiologically possible in calculating insulin doses.

20. The method of claim 11, further comprising utilizing glucose levels from past dosing intervals in calculating insulin doses.

* * * * *